(12) United States Patent
Shankar et al.

(10) Patent No.: US 6,310,256 B1
(45) Date of Patent: Oct. 30, 2001

(54) SYNTHESIS OF 4-KETOCYCLOPENTENE COMPOUNDS

(75) Inventors: Ravi B. Shankar; Francis J. Timmers, both of Midland, MI (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/443,394

(22) Filed: Nov. 19, 1999

Related U.S. Application Data

(60) Provisional application No. 60/122,614, filed on Mar. 3, 1999.

(51) Int. Cl.$^7$ .................................................. C07C 49/597
(52) U.S. Cl. ............................................ 568/314; 568/346
(58) Field of Search ..................................... 568/309, 312, 568/314, 319, 346

(56) References Cited

U.S. PATENT DOCUMENTS

| | | | |
|---|---|---|---|
| 2,656,390 | 10/1953 | Max | 260/586 |
| 4,985,576 | 1/1991 | Rohrmann et al. | 556/435 |
| 5,597,935 | 1/1997 | Jordan et al. | 556/11 |
| 5,646,083 | 7/1997 | Van Beek | 502/104 |
| 5,703,187 | 12/1997 | Timmers | 526/282 |

FOREIGN PATENT DOCUMENTS

| | | |
|---|---|---|
| A-563365 | 4/1993 | (WO) . |
| WO 99 14221 A | 3/1999 | (WO) . |
| WO 99 40096 A | 8/1999 | (WO) . |

OTHER PUBLICATIONS

Arthur C. Cope et al., *JACS*, Jun. 5, 1996, pp. 2547–2551, vol. 78.

Arthur C. Cope et al., "The condensation product 9, 10–phenanthrenequinone and ethyl acetoacetate", Journal of the American Chemical Society, pp. 5513–5516 (1958).

R. M. Cooper et al., "Acetolysis of 2–(2, 3–dihydro–1H–cyclopenta '1! Phenanthren–2–Y1) ethyL derivatives: participating by the 9, 10–bond of phenanthrene to give an analog of a classical norbornyl cation", 1972, J. Chem. Soc., pp. 594–598.

*Primary Examiner*—Sreeni Padmanabhan

(57) ABSTRACT

A process for forming 4-ketocyclopentene and substituted 4-ketocyclopentene compounds starting from the corresponding 1-carbohydrocarbyloxy-2-keto-4-hydroxy-5-cyclopentene by reduction followed by decarboxylation.

3 Claims, No Drawings

SYNTHESIS OF 4-KETOCYCLOPENTENE COMPOUNDS

CROSS REFERENCE

This application claims benefit of priority from provisional application No. 60/122,614, filed Mar. 3, 1999.

FIELD OF THE INVENTION

This invention relates to the synthesis of 4-ketocyclopentene compounds including further substituted derivatives thereof, and their conversion to cyclopentadiene compounds or substituted cyclopentadiene compounds, which are useful chemicals, particularly in the synthesis of cyclopentadienyl containing metal complexes useful in addition polymerization catalyst compositions. Group 4 metal complexes containing the foregoing cyclopentadienyl ligands are especially suited for use in catalyst compositions for the homopolymerization of ethylene or propylene and the copolymerization of ethylene with an α-olefin. The present process is particularly suitable for use in the industrial scale preparation of 4-ketocyclopentene or substituted 4-ketocyclopentene compounds, cyclopentadiene or substituted cyclopentadiene derivatives thereof, and in the synthesis of cyclopentadienyl or substituted cyclopentadienyl containing metal complexes therefrom.

BACKGROUND

The preparation of cyclopentadiene compounds from various starting materials is well known. Metal complexes containing cyclopentadienyl or substituted cyclopentadienyl ligands are also well known. Several techniques for preparing such ligands are disclosed in U.S. Pat. No. 5,703,187, 4,985,576, 5,646,083, 5,597,935, and EP-A-563365. In copending application Ser. No. 08/122958, filed Jul. 27, 1998, the preparation of certain 1 H-cyclopenta(/)ophenanthrene containing metal complexes and their use in addition polymerization catalyst compositions is disclosed and claimed. The technique for preparing such complexes disclosed by the reference started with 1H-cyclopenta-(I)phenanthrene. In *JACS*, 78, 2547–2551 (1956), a synthetic scheme for preparing 1H-cyclopenta(I)phenanthrene, the ultimate step involving dehydration of 2,3-dihydro-2-oxo-1H-cyclopenta(I)phenanthrene with boric acid was disclosed. Disadvantageously, this particular procedure resulted in low yields and insufficient purity of the resulting ligand group containing compounds.

Previously known synthetic procedures involved multiple unit operations, thereby making the process less efficient than desired. Accordingly, it would be desirable if there were provided a process for preparing 4-ketocyclopentene or substituted 4-ketocyclopentene compounds and cyclopentadiene or substituted cyclopentadiene derivatives thereof in higher yields and purity.

SUMMARY OF THE INVENTION

According to the present invention there is provided a process for forming 4-ketocyclopentene and substituted 4-ketocyclopentene compounds starting from the corresponding 1-carbohydrocarbyloxy-2-keto-4-hydroxy-5-cyclopentene by reduction followed by decarboxylation. Preferably, the reduction is occasioned by reaction of the initial compound with a metal, preferably zinc. The decarboxylation is preferably conducted by further reaction of the intermediate with an inorganic halide compound and one or more organic acids under hydrolysis and condensation conditions. The reduction and decarboxylation may be conducted simultaneously or sequentially in the same reactor or in different reactors. Preferably the carboxylate compound is contacted with zinc in the presence of a mixture of an organic acid and hydrochloric acid.

The foregoing procedure is illustrated schematically as follows:

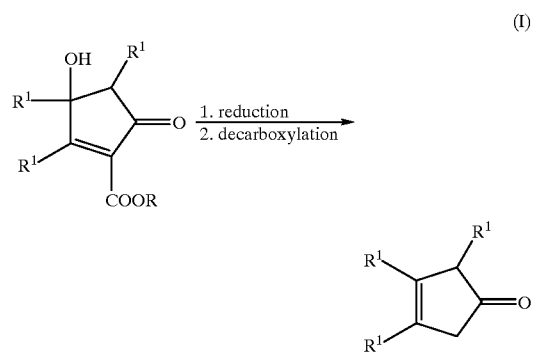

wherein, R is $C_{1-20}$ hydrocarbyl, preferably $C_{1-4}$ alkyl; and $R^1$ independently each occurrence is hydrogen, hydrocarbyl, silyl, germyl, halide, or halo- substituted hydrocarbyl, said $R^1$ group having up to 40 atoms not counting hydrogen atoms, and optionally two or more of the foregoing adjacent $R^1$ groups may together form a divalent derivative thereby forming a saturated or unsaturated fused ring or multiple ring system, and further optionally one or more of the carbons of $R^1$ in any of the so formed rings may be replaced by a nitrogen, boron, phosphorus or sulfur atom.

Beneficially, the foregoing improved process incorporates multiple chemical transformations into a single step process thereby significantly improving the efficiency of the preparation.

In a further embodiment of the present invention the resulting ketone is converted to a cyclopententadiene or substituted cyclopentadiene compound by a series of reactions which beneficially may be performed sequentially in the same reactor or in multiple reactors. In the process the ketone is reduced to form an intermediate alcohol, the hydroxyl functionality is replaced under substitution conditions with a leaving group or otherwise converted to a leaving group, and the resulting product is deprotonated under base induced elimination conditions to form the cyclopentadiene compound. If desired, a suitable functional substituent may be incorporated simultaneously with the elimination step. This process is illustrated schematically as follows:

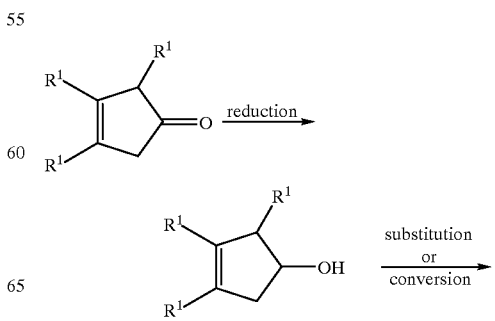

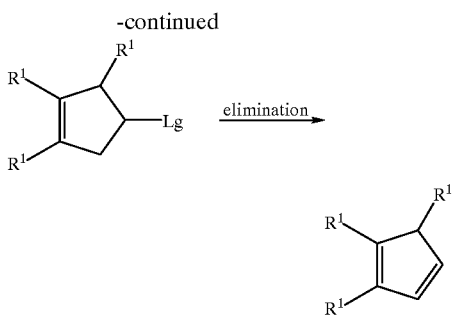

wherein $R^1$ is as previously defined, and
Lg is a suitable ligand group that is subject to base induced elimination. Preferred Lg groups are: halo, silyl, $OSO_2R^6$, —$Si(R^5)_2$—, —$Si(R_5)_2N(R^5)_2)$, or —$Si(R^5)_2N(R^5)$— groups, wherein $R^5$ is a $C_{1-20}$ aliphatic or cycloaliphatic group, and $R^6$ is $R^5$ or a $C_{6-20}$ aryl group or sulfonate ester such as tosyl or mesyl. Most preferably, Lg is halo, especially bromo.

When further cyclopentadienyl substituted compounds are desired, the final elimination step may be followed by further substitution of Lg with a functional substituent or even formation of dimeric bridged ligands through a coupling of ligand groups, utilizing techniques well known to the skilled artisan. Highly preferred functional substituents include metals, hydrocarbyl, silyl, hydrocarbyl- or polyhydrocarbyl- substituted silyl, silyl- or polysilyl- substituted hydrocarbyl groups, metallated derivatives of such hydrocarbyl, silyl, substituted silyl or subsitituted hydrocarbyl groups, or bridging groups of the formula: —Z'Y— when a coupled product is formed, or masked, metallated, or coupled derivatives thereof, said functional substituent having up to 50 atoms not counting hydrogen, wherein:

Y is —O—, —S—, —$NR^5$—, —$PR^5$—;

—$NR^5_2$, —$PR^5_2$, or

Z' is $SiR^5_2$, $CR^5_2$, $SiR^5_2SiR^5_2$, $CR^5_2CR^5_2$, $CR^5$=$CR^5$, $CR^5_2SiR^5_2$, $BR^5$, B=$NR^5_2$, or $GeR^5_2$; and $R^5$ each occurrence is independently hydrogen, or a member selected from hydrocarbyl, hydrocarbyloxy, silyl, halogenated alkyl, halogenated aryl, and combinations thereof, said $R^5$ having up to 20 non-hydrogen atoms, and optionally, two $R^5$ groups from Z' (when $R^5$ is not hydrogen), or an $R^5$ group from Z' and an $R^5$ group from Y form a ring system.

Masked derivatives of the foregoing ligands are those ligands containing an easily removable group at the position desired for later coupling or further functionalization of the compound. An example is a trihydrocarbylsilyl group, especially trimethylsilyl. In a highly preferred embodiment of the invention the foregoing Lg group is replaced with the desired functional ligand group in a single step which is a combination of elimination, deprotonation and replacement operations using two equivalents of base for each equivalent of cyclopentediene compound and the addition of the source for the functional group, $R^7Fs$, where $R^7$ is a leaving group, preferably halogen or a sulfonate ester, and Fs is a functional substituent, preferably —Z'YH. Because the combination of three processes in one step does not involve dehydration of an alcohol intermediate, formation of dimeric byproducts through a Diels-Alder reaction of the diene is avoided. This combined process may be illustrated schematically as follows:

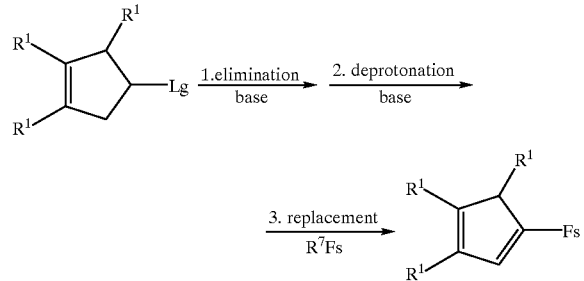

Finally according to the present invention there is provided a process for preparing metal complexes comprising cyclopentadienyl- or substituted cyclopentadienyl- ligands using one or all of the foregoing intermediate process steps. The present processes result in the highly efficient production of metal complexes and metal complex intermediates.

DETAILED DESCRIPTION OF THE INVENTION

All reference to the Periodic Table of the Elements herein shall refer to the Periodic Table of the Elements, published and copyrighted by CRC Press, Inc., 1995. Also, any reference to a Group or Groups shall be to the Group or Groups as reflected in this Periodic Table of the Elements using the IUPAC system for numbering groups. The term "hydrocarbyl" where used generically includes alkyl, aryl, cycloalkyl, aralkyl and alkaryl groups. Where any reference herein is made to any patent, patent application or publication, the teachings are hereby incorporated by reference herein.

The hydrolysis and condensation reactions are suitably performed in a diluent comprising a mixture of one or more organic acids and one or more inorganic halides at a temperature from 0 to 200° C., preferably 50–150° C. A preferred organic acid is acetic acid. A preferred acid mixture is a combination of glacial acetic acid and concentrated hydrochloric acid, most preferably in a volume of 10/1 to 1/1. Preferably the metal is finely comminuted, uniformly dispersed in the acid mixture, and used in approximately an equimolar ratio with the ketoester. The ketone product is suitably recovered by adding the mixture to water, cooling and recovering the product by separation from the aqueous mixture.

The reduction of the ketone can be accomplished using sodium borohydride or similar reducing agent in a solvent or diluent at a temperature from 0 to 150° C., followed by quenching with an acid. A suitable diluent mixture is a chloroform/ethanol mixture, preferably in a volume ratio from 10/50 to 90/10, most preferably about 50/10. The final steps of substitution and elimination may be conducted at temperatures from 0 to 150° C. using multiple steps or combining the separate steps. The initial substitution is desirable conducted in the presence of an acid acceptor such as pyridine. Highly desirably, the hydroxyl group is first converted to a sulfonic acid ester by reaction with, methanesulfonyl chloride which is readily converted to the halide by reaction with a metal halide such as lithium bromide. The foregoing steps are desirably conducted in the presence of an organic solvent, such as methylenechloride for the first step and acetone for the second step. The final step in formation of the cyclopentadiene or cyclopentadienyl ligand uses standard organometallic techniques, generally metalization or similar metathesis reactions depending on the desired final product. The skilled artisan will appreciate that the final step of elimination (or deprotonation) may be combined with a functionalizing step if desired. When the preferred combination of elimination/deprotonation, and replacement operations are performed in one step, two or more equivalents of a base, preferably from 2 to 2.5 equivalents, are used to cause both elimination and deprotonation, and the functionalizing reagent, $R^7Fs$ is added after the deprotonation step is completed or substantially completed. A preferred functionalizing reagent is $R^7$—Z'Y—H.

The present process has proven to be highly desirable in the formation of certain bulky multiring cyclopentadiene derivatives, specifically 1H-cyclopenta(I) phenanthrene derivatives. Especially desirable is its use in a process for forming 2,3-dihydro-2-oxo-1H-cyclopenta(I)phenanthrene by reaction of an alkyl 3,3a-dihydro-3a-hydroxy-2-oxo-2H-cyclopenta(I)phenanthrene-1-carboxylate. This may be illustrated schematically as follows:

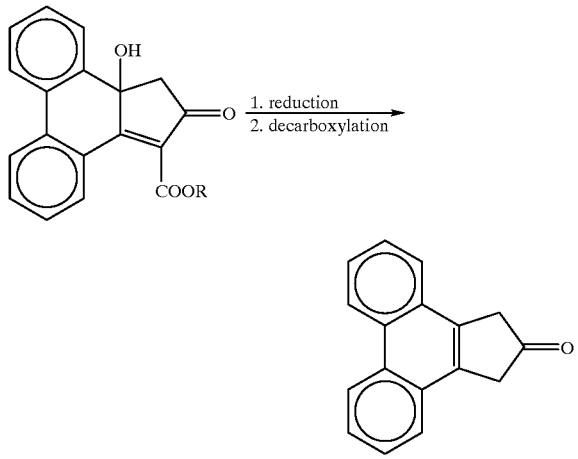

wherein R is as previously defined.

In the subsequent steps, the ketone is converted to a 2,3-dihydro-2-substituted-(1H)cyclopenta(I)phenanthrene ligand, as follows:

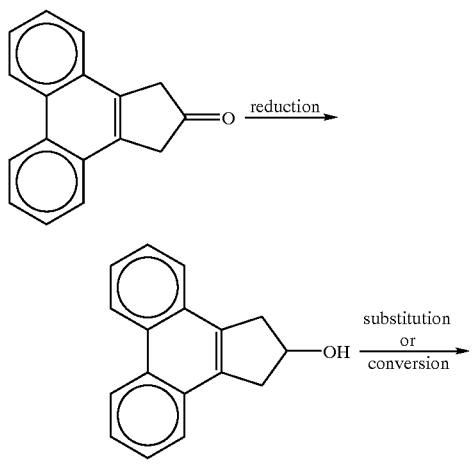

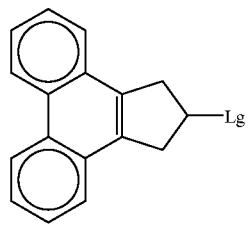

wherein Lg is as previously defined.

In the final steps, the 2,3-dihydro-2'-substituted-1H-cyclopenta(I)phenanthrene compound may be converted to the desired ligand group for further synthesis using standard metalizing and substitution procedures.

Alkyl 3,3a-dihydro-3a-hydroxy-2-oxo-2H-cyclopenta(I) phenanthrene-1-carboxylate compounds for use in the foregoing procedure are prepared according to known techniques. One suitable technique is condensation of 9,10-phenanthrene quinone with an alkyl acetoacetate, such as methyl acetoacetate or ethyl acetoacetate, in the presence of an acid acceptor such as piperidine. The initial 9,10-phenanthrene quinone, if not available commercially, may be readily prepared by reaction of phenanthrene with excess acetic acid in the presence of an oxidizing agent such as potassium bromate. The foregoing synthetic procedures are illustrated as follows:

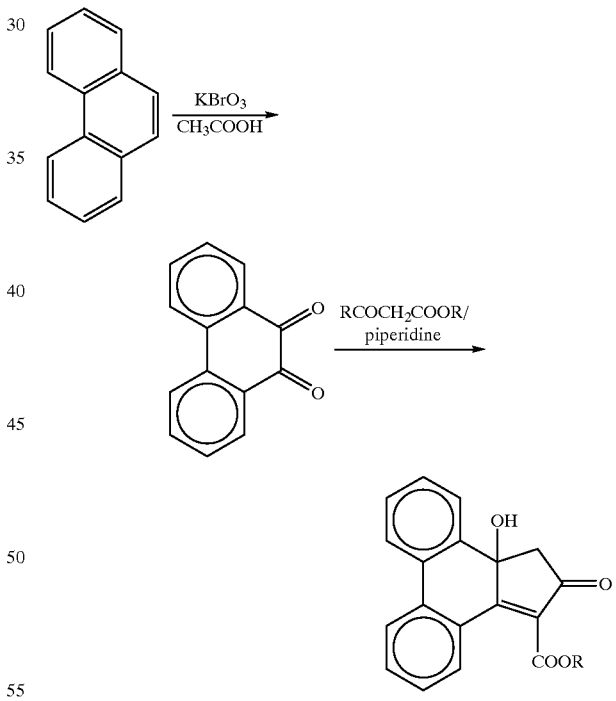

wherein R is as previously defined.

As previously mentioned, the foregoing syntheses are useful in preparing ligands for metal complexes that are components of addition polymerization catalyst compositions. Preferred metal complexes generally correspond to the formula: $CpZMX_xL_lX'_{x'}$ (IA);

where Cp is a cyclopentadienyl ligand derived from the foregoing cyclopentadienyl or substituted cyclopentadienyl compounds;

M is titanium, zirconium or hafnium in the +2, +3 or +4 formal oxidation state;

Z is either a cyclic or noncyclic ligand group containing delocalized π-electrons, including a second cyclopentadienyl ring system group as herein previously disclosed for Cp, said Z being bonded to M by means of delocalized π-electrons and optionally covalently bonded to Cp through a divalent bridging group, or Z is a divalent moiety lacking in delocalized π-electrons that is covalently bonded to Cp and M, or such a moiety comprising one σ-bond by which it is bonded to Cp, and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms other than hydrogen;

L independently each occurrence is a neutral ligand having up to 20 atoms;

X' is a divalent anionic ligand group having up to 60 atoms;

x is 0, 1, 2, or 3;

l is a number from 0 to 2, and x' is 0 or 1.

The above complexes may exist as isolated crystals optionally in pure form, or as a mixture with other complexes, in the form of a solvated adduct, optionally in a solvent, especially an organic liquid, as well as in the form of a dimer or chelated derivative thereof, wherein the chelating agent is an organic material such as ethylenediaminetetraacetic acid (EDTA).

The catalyst compositions for olefin polymerization generally comprise:

A.
  1) a metal complex of formula (IA), and
  2) an activating cocatalyst, the molar ratio of 1) to 2) being from 1:10,000 to 100:1, or B.
  the reaction product formed by converting a metal complex of formula (IA) to an active catalyst by use of an activating technique.

The olefin polymerization processes generally comprise contacting one or more $C_{2-20}$ α-olefins under polymerization conditions with a catalyst comprising:

A.
  1) a metal complex of formula (IA), and
  2) an activating cocatalyst, the molar ratio of 1) to 2) being from 1:10,000 to 100:1, or B.
  the reaction product formed by converting a metal complex of formula (IA) to an active catalyst by use of an activating technique.

The catalyst compositions may also be supported on a support material and used in olefin polymerization processes in a slurry or in the gas phase. The catalyst may be prepolymerized with one or more olefin monomers in situ in a polymerization reactor or in a separate process with intermediate recovery of the prepolymerized catalyst prior to the primary polymerization process.

Highly preferred metal complexes prepared by using the cyclopentadiene compounds prepared by the present process correspond to the formula:

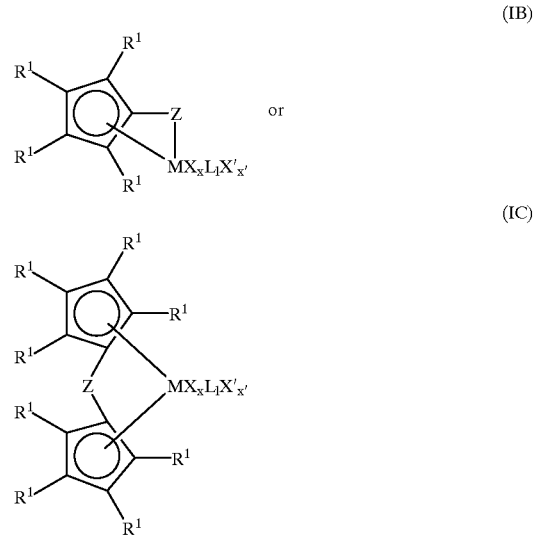

where M is titanium, zirconium or hafnium in the +2, +3 or +4 formal oxidation state;

$R^1$ independently each occurrence is hydrogen, hydrocarbyl, silyl, germyl, halide, hydrocarbyloxy, hydrocarbylsiloxy, hydrocarbylsilylamino, di(hydrocarbyl)amino, hydrocarbyleneamino, di(hydrocarbyl)phosphino, hydrocarbylene-phosphino, hydrocarbylsulfido, halo- substituted hydrocarbyl, hydrocarbyloxy- substituted hydrocarbyl, silyl- substituted hydrocarbyl, hydrocarbylsiloxy- substituted hydrocarbyl, hydrocarbylsilylamino- substituted hydrocarbyl, di(hydrocarbyl)amino- substituted hydrocarbyl, hydrocarbyleneamino-substituted hydrocarbyl, di(hydrocarbyl)phosphino- substituted hydrocarbyl, hydrocarbylenephosphino- substituted hydrocarbyl, or hydrocarbylsulfido- substituted hydrocarbyl, said $R^1$ group having up to 40 atoms not counting hydrogen atoms, and optionally two or more of the foregoing adjacent $R^1$ groups may together form a is divalent derivative thereby forming a saturated or unsaturated fused ring, and further optionally one or more of the carbons of any of the rings may be replaced by a nitrogen or sulfur atom;

Z is a divalent moiety lacking in delocalized π-electrons, or such a moiety comprising one σ-bond and a neutral two electron pair able to form a coordinate-covalent bond to M, said Z comprising boron, or a member of Group 14 of the Periodic Table of the Elements, and also comprising nitrogen, phosphorus, sulfur or oxygen;

X is a monovalent anionic ligand group having up to 60 atoms exclusive of the class of ligands that are cyclic ligand groups bound to M through delocalized π-electrons;

L independently each occurrence is a neutral ligating compound having up to 20 atoms;

X' is a divalent anionic ligand group having up to 60 atoms;

x is 0, 1, 2, or 3;

l is a number from 0 to 2, and x' is 0 or 1.

In the metal complexes, preferred L groups are carbon monoxide; phosphines, especially trimethylphosphine, triethylphosphine, triphenylphosphine and bis(1,2- dimethylphosphino)ethane; $P(OR^4)_3$, wherein $R^4$ is $C_{1-20}$ hydrocarbyl; ethers, especially tetrahydrofuran; amines, especially pyridine, bipyridine, tetramethylethylenediamine (TMEDA), and triethylamine; olefins; and neutral conjugated dienes having from 4 to 40, preferably 5 to 40 carbon atoms. Complexes including such neutral diene L groups are those wherein the metal is in the +2 formal oxidation state.

Further in reference to the metal complexes, X preferably is selected from the group consisting of hydro, halo, hydrocarbyl, silyl, and N,N-dialkylamino- substituted hydrocarbyl. The number of X groups depends on the oxidation state of M, whether Z is divalent or not and whether any neutral diene groups or divalent X' groups are present. The skilled artisan will appreciate that the quantity of the various substituents and the identity of Z are chosen to provide charge balance, thereby resulting in a neutral metal complex. For example, when Z is divalent, and x is zero, x' is two less than the formal oxidation state of M. When Z contains one neutral two electron coordinate-covalent bonding site, and M is in a formal oxidation state of +3, x may equal zero and x' equal 1, or x may equal 2 and x' equal zero. In a final example, if M is in a formal oxidation state of +2, Z may be a divalent ligand group, whereupon x and x' are both equal to zero and one neutral L ligand group may be present.

The complexes can be prepared by combining a Group 4 metal tetrahalide or tetraamide salt with the corresponding cyclopentadienyl ring system ligand dianion in an inert diluent. Optionally a reducing agent can be employed to produce the lower oxidation state complexes, and standard ligand exchange procedures can by used to produce different ligand substituents.

Processes that are suitably adapted for use herein are well known to synthetic organometallic chemists. The synthesis of the cyclopentadiene compounds, derivatives thereof, and metal complexes, and all other preparations herein, unless stated to the contrary, are conducted in a suitable noninterfering solvent at a temperature from −100 to 300° C., preferably from −80 to 150° C., most preferably from 0 to 50° C. By the term "reducing agent" herein is meant a metal or compound which, under reducing conditions causes the metal M, to be reduced from a higher to a lower oxidation state, or for organic syntheses, causes addition of hydrogen to the compound. Examples of suitable metal reducing agents are alkali metals, alkaline earth metals, aluminum and zinc, alloys of alkali metals or alkaline earth metals such as sodium/mercury amalgam and sodium/potassium alloy. Examples of suitable reducing agent compounds are sodium naphthalenide, potassium graphite, lithium alkyls, lithium or potassium alkadienyls; and Grignard reagents. Most preferred reducing agents are the alkali metals or alkaline earth metals, especially lithium and magnesium metal. By the term "oxidizing agent" herein is meant a metal or compound which causes the metal M, to be oxidized from a lower to a higher oxidation state, or for organic syntheses, causes addition of oxygen to the compound. Suitable oxidizing agents for organometallic oxidations include chlorinated hydrocarbons, especially methylenechloride. Suitable oxidizing agents for organic syntheses include potassium bromate.

Suitable reaction media for the formation of the complexes include aliphatic and aromatic hydrocarbons, ethers, and cyclic ethers, particularly branched-chain hydrocarbons such as isobutane, butane, pentane, hexane, heptane, octane, and mixtures thereof; cyclic and alicyclic hydrocarbons such as cyclohexane, cycloheptane, methylcyclohexane, methylcycloheptane, and mixtures thereof; aromatic and hydrocarbyl-substituted aromatic compounds such as benzene, toluene, and xylene, $C_{1-4}$ dialkyl ethers, $C_{1-4}$ dialkyl ether derivatives of (poly)alkylene glycols, and tetrahydrofuran. Mixtures of the foregoing are also suitable. All of the foregoing steps are conducted according to well known organic or organometallic synthetic techniques.

The complexes are rendered catalytically active by combination with an activating cocatalyst or by use of an activating technique. Suitable activating cocatalysts for use herein include polymeric or oligomeric alumoxanes, especially methylalumoxane, triisobutyl aluminum modified methylalumoxane, or isobutylalumoxane; neutral Lewis acids, such as $C_{1-30}$ hydrocarbyl substituted Group 13 compounds, especially tri(hydrocarbyl)aluminum- or tri (hydrocarbyl)boron compounds and halogenated (including perhalogenated) derivatives thereof, having from 1 to 10 carbons in each hydrocarbyl or halogenated hydrocarbyl group, more especially perfluorinated tri(aryl)boron compounds, and most especially tris(pentafluorophenyl) borane; nonpolymeric, compatible, noncoordinating, ion forming compounds (including the use of such compounds under oxidizing conditions), especially the use of ammonium-, phosphonium-, oxonium-, carbonium-, silylium- or sulfonium- salts of compatible, noncoordinating anions, or ferrocenium salts of compatible, noncoordinating anions; bulk electrolysis (explained in more detail hereinafter); and combinations of the foregoing activating cocatalysts and techniques. The foregoing activating cocatalysts and activating techniques have been previously taught with respect to different metal complexes in the following references: U.S. Pat. Nos. 5,153,157, 5,064,802, 5,321,106, 5,350,723, and EP-A-520,732 (equivalent to U.S. Ser. No. 07/876,268), the teachings of which are hereby incorporated by reference.

Combinations of neutral Lewis acids, especially the combination of a trialkyl aluminum compound having from 1 to 4 carbons in each alkyl group and a halogenated tri (hydrocarbyl)boron compound having from 1 to 20 carbons in each hydrocarbyl group, especially tris (pentafluorophenyl)borane, further combinations of such neutral Lewis acid mixtures with a polymeric or oligomeric alumoxane, and combinations of a single neutral Lewis acid, especially tris(pentafluorophenyl)borane with a polymeric or oligomeric alumoxane are especially desirable activating cocatalysts. Preferred molar ratios of Group 4 metal complex:tris(pentafluorophenyl-borane:alumoxane are from 1:1:1 to 1:5:20, more preferably from 1:1:1.5 to 1:5:10.

Suitable ion forming compounds useful as cocatalysts in one embodiment of the present invention comprise a cation which is a Bronsted acid capable of donating a proton, and a compatible, noncoordinating anion, $A^-$. As used herein, the term "noncoordinating" means an anion or substance which either does not coordinate to the Group 4 metal containing precursor complex and the catalytic derivative derived therefrom, or which is only weakly coordinated to such complexes thereby remaining sufficiently labile to be displaced by a neutral Lewis base. A noncoordinating anion specifically refers to an anion which when functioning as a charge balancing anion in a cationic metal complex does not transfer an anionic substituent or fragment thereof to said cation thereby forming neutral complexes. "Compatible anions" are anions which are not degraded to neutrality when the initially formed complex decomposes and are noninterfering with desired subsequent polymerization or other uses of the complex.

Preferred anions are those containing a single coordination complex comprising a charge-bearing metal or metalloid core which anion is capable of balancing the charge of the active catalyst species (the metal cation) which may be formed when the two components are combined. Also, said anion should be sufficiently labile to be displaced by olefinic, diolefinic and acetylenically unsaturated compounds or other neutral Lewis bases such as ethers or nitrites. Suitable metals include, but are not limited to, aluminum, gold and platinum. Suitable metalloids include, but are not limited to, boron, phosphorus, and silicon. Compounds containing anions which comprise coordination complexes containing a single metal or metalloid atom are, of course, well known and many, particularly such compounds containing a single boron atom in the anion portion, are available commercially.

Preferably such cocatalysts may be represented by the following general formula:

(L*—H)⁺(A)⁻ 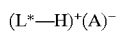

wherein:

L* is a neutral Lewis base;

(L*—H)⁺ is a conjugate Bronsted acid of L*; and

A⁻ is a noncoordinating, compatible anion having a charge of −1.

More preferably A⁺ corresponds to the formula: $[M'Q_4]^-$;
wherein:

M' is boron or aluminum in the +3 formal oxidation state; and

Q independently each occurrence is selected from hydride, dialkylamido, halide, hydrocarbyl, hydrocarbyloxide, halosubstituted-hydrocarbyl, halo-substituted hydrocarbyloxy, and halo- substituted silyl-hydrocarbyl radicals (including perhalogenated hydrocarbyl- perhalogenated hydrocarbyloxy- and per-halogenated silylhydrocarbyl radicals), said Q having up to 20 carbons with the proviso that in not more than one occurrence is Q halide. Examples of suitable hydrocarbyloxide Q groups are disclosed in U.S. Pat. No. 5,296,433, the teachings of which are herein incorporated by reference.

Activating cocatalysts comprising boron which are particularly useful in the preparation of catalyst compositions may be represented by the following general formula:

(L*—H)⁺(BQ₄)⁻; 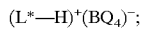

wherein:

L* is as previously defined;

B is boron in a formal oxidation state of 3; and

Q is a hydrocarbyl-, hydrocarbyloxy-, fluorinated hydrocarbyl-, fluorinated hydrocarbyloxy-, or fluorinated silylhydrocarbyl- group of up to 20 nonhydrogen atoms, with the proviso that in not more than one occasion is Q hydrocarbyl.

Preferred Lewis base salts are ammonium salts, more preferably trialkylammonium salts containing one or more $C_{12-40}$ alkyl groups, most preferably methyldioctadecylammonium or dimethyloctadecylammonium salts. Most preferably, Q is each occurrence an inertly substituted aryl group, especially, a pentafluorophenyl or p-dialkylaluminoxyphenyl.

EXAMPLES

The skilled artisan will appreciate that the invention disclosed herein may be practiced in the absence of any component which has not been specifically disclosed. The following examples are provided as further illustration of the invention and are not to be construed as limiting. Unless stated to the contrary all parts and percentages are expressed on a weight basis. All syntheses of air or water sensitive compounds were performed under dry nitrogen or argon atmosphere using a combination of glove box and high vacuum techniques. Solvents were purified by passing through double columns charged with activated alumina and a purification catalyst (Q-5® catalyst available from Englehardt Corporation). The term "overnight", if used, refers to a time of approximately 16–18 hours, "room temperature", if used, refers to a temperature of about 20–25 °C., and "mixed alkanes" refers to a mixture of mostly $C_6-C_{12}$ alkanes available commercially under the trademark Isopar E™ from Exxon Chemicals Inc.

Example 1

Synthesis of 2,3-dihydro-2-oxo-1H-cyclopenta(I) phenanthrene (1) Preparation of Phenanthrenequinone

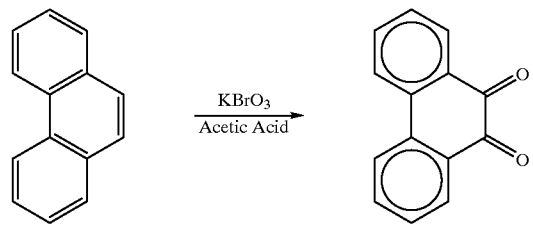

Phenanthrene (16 g, Aldrich Tech Grade (90 percent), 0.081 mol) and acetic acid (200 ml) were stirred and heated to 70–75° C. Potassium bromate (32 g, 0.19 mol) was added in 2 portions. After the addition of the first portion the temperature rose to reflux with evolution of bromine vapors. The second portion was added and the condenser was replaced by a distillation head. The heating was continued until the distillate was colorless. The deep red solution was cooled and poured into water (300 ml) and the precipitate was isolated by filtration. The crude product was purified by reslurrying in 100 ml of hot (70° C.) aqueous sodium bisulfite solution (40 percent) and filtering while hot. The deep red filtrate was cooled and treated with aqueous sodium carbonate until basic. The precipitated product was recovered by extraction with methylene chloride, dried and concentrated to yield 13.4 g (80 percent yield) of orange yellow solid: mp 182–184° C.

(2) Preparation of 2,11b-dihydro-11b-hydroxy-2-oxo-1H-cyclopenta[I]phenanthrene-3-carboxylic acid methyl ester

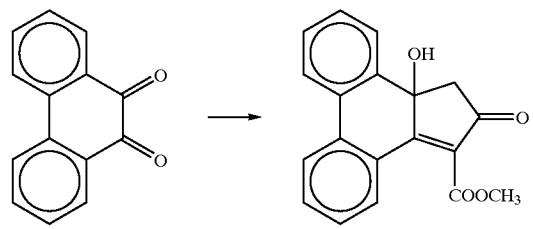

A slurry of phenanthrenequinone (10.5 g, 0.05 mol) in ethanol (60 ml) containing methyl acetoacetate (6.96 g, 0.06 mol) and piperidine (6–8 drops) was refluxed for 2 to 2.5 h. The quinone eventually dissolved and the entire reaction mixture solidified. Filtration of the cooled mixture gave 14.3 g (93 percent) of a white solid: $^1$H NMR (CDCl$_3$,δ) 3.21 (d of d, 2H, J=18 Hz), 3.87(s, 3H), 7.3–8.0(m, 8H).

(3) Preparation of 1,3-Dihydro-2H-Cyclopenta[I]phenanthrene-2-one

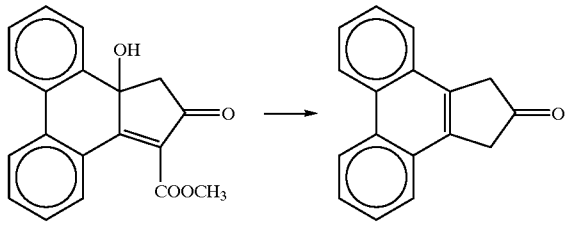

The ketoester of step 2 (14.1 g, 0.046 mol) was added to a mixture of acetic acid (150 ml) and hydrochloric acid (5 ml) containing zinc dust (6 g, 0.092 mol). The mixture immediately solidified. The mixture was slowly heated to reflux when all the solids dissolved giving a clear yellow solution containing unreacted zinc granules. The mixture was refluxed for 4 h and filtered while hot. The filtrate was cooled and poured into ice water. The resulting white precipitate was filtered and dried. A small amount of the product that had crystallized out during the hot filtration was recovered by extraction with methylene chloride and concentrating to yield the product. The combined yield was 10.4 g (97.3 percent). $^1$H NMR (CDCl$_3$, δ) 3.71(s, 4H), 7.62(bs, 6H), 8.68(d, 2H, J=7 Hz).

(4) Preparation of 2,3-Dihydro-1H-Cyclonenta[I]phenanthrene-2-ol

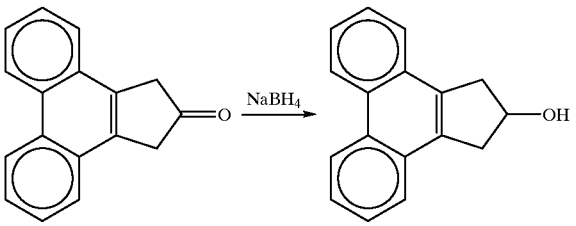

Sodium borohydride (1 g, 0.027 mol) was added to a slurry of 2,3-Dihydro-2H-Cyclopenta[I]phenanthrene-2-one (4.6 g, 0.02 mol) in 50 ml of chloroform and 10 ml of ethanol. The resulting yellow solution was stirred overnight and quenched with 10 percent aqueous HCl. The mixture was transfered to a separatory funnel and the organic layer was washed with saturated sodium bicarbonate solution, dried over anhydrous magnesium sulfate and concentrated under reduced pressure to yield the product as a yellowish white solid. Yield was 4.7 g, 100 percent). $^1$H NMR (CDCl$_3$-DMSO -d$_6$, δ) 3.31 (d, 2H, J=16 Hz), 3.56 (d of d, 2H, J=16, 6 Hz), 4.76 (brs, 1H), 4.91 (brs, 1H), 7.59–7.85 (m, 6H), 8.67–8.70 (m, 2H).

(5) Preparation of 2,3-Dihydro-1H-Cyclopenta[I]phenanthrene-2-ol methanesulfonate

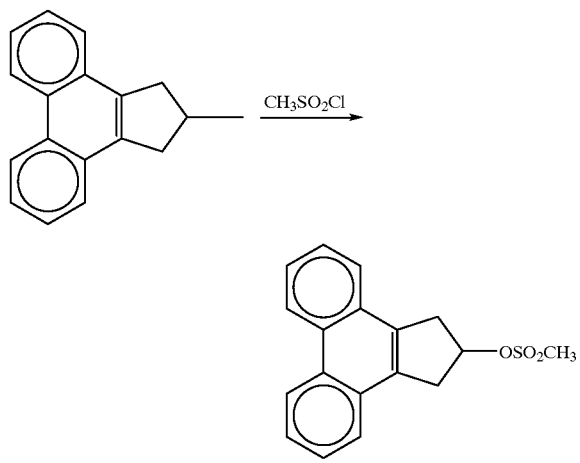

To a stirred suspension of 2,3-dihydro-1H-cyclopentaphenanthrene-2-ol (2.34 g, 0.01 mol) in 20 ml of pyridine was added a solution of methanesulfonyl chloride (2.28 g, 0.02 mol) in 15 ml of methylene chloride and allowed to stir a for 2 hr at room temperature. The reaction mixture was worked up by washing with 10 percent aqueous HCl, drying over anhydrous magnesium sulfate and concentrating under reduced pressure to yield the methanesulfonate as a tan solid (3.11 g, 100 percent). $^1$H NMR (CDCl$_3$, δ) 3.05 (s, 3H), 3.58–3.69 (m, 4H), 5.75 (m, 1H), 7.60–7.76 (m, 6H), 8.68 (m, 2H).

(6) Preparation of 2-Bromo-2,3-Dihydro-1H-Cyclopenta[I]phenanthrene

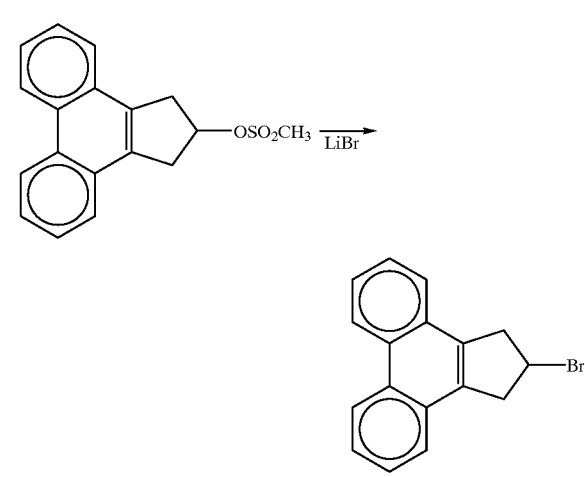

A mixture of 2,3-Dihydro-1H-Cyclopenta[I]phenanthrene-2-ol methanesulfonate (3.11 g, 0.01 mol) and lithium bromide( 2.61 g, 0.03 mol) in 50 ml of acetone was refluxed for 18 hr. The reaction mixture was worked up by concentrating to remove the volatiles and extracting with a mixture of methylene chloride and hexane(1:3) and filtering through silica gel to yield 2.34 g (80 percent) of the bromide as a buff colored solid. $^1$H NMR (CDCl$_3$, δ) 3.73–3.94 (m,4H), 4.97 (m, 1H), 7.58–7.76 (m, 6H), 8.66 (m, 2H); $^{13}$C NMR (CDCl$_3$, δ) 44.34, 47.28, 123.20, 124.69, 126.07, 126.83, 129.17, 130.38, 134.40.

(7) Preparation of (1H-Cyclopenta[I]phenanthrene-2-yl)dimethyl(t-butylamino)silane

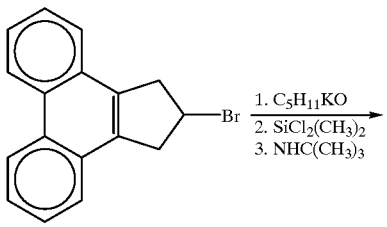

1. C$_5$H$_{11}$KO
2. SiCl$_2$(CH$_3$)$_2$
3. NHC(CH$_3$)$_3$

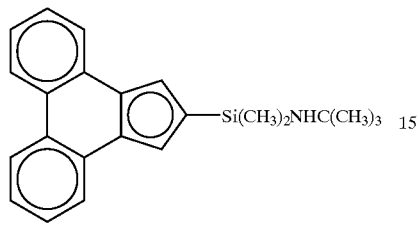

To a solution of 2-bromo-cyclopentaphenanthrene (0.500 g, 1.68 mmol) in 40 mL THF was added 25 percent (wt/wt) potassium amylate in cyclohexane (2.0 g, 3.7 mmol). The solution color changed to orange immediately and a precipitate formed. The mixture was heated to reflux. After 30 minutes heating the mixture was cooled and the volatile materials were removed under reduced pressure. The residue was slurried in 30 mL THF and this mixture was added slowly to neat dichlorodimethylsilane (2.0 mL, 17 mmol). The resulting mixture was pale yellow. Fifteen minutes after the addition was complete, volatile materials were removed under reduced pressure. The residue was slurried in 30 mL THF and tert-butylamine was added to the resulting mixture which was left to stir overnight. The volatile materials were removed under reduced pressure and the resulting residue was extracted three times with a total of 60 mL of mixed hexanes. The extracts were filtered and volatile materials were removed from the combined filtrates under reduced pressure. The product was formed as white crystals upon cooling. Yield of the desired product was 0.575 g, 99 percent.

What is claimed is:

1. A process for forming a 4-ketocyclopentene compound comprising reducing a 1-carbohydrocarbyloxy-2-keto-4-hydroxy-5-cyclopentene compound by contacting with zinc and decarboxylating the resulting reaction product by contacting the reaction mixture with a mixture of an organic acid and an inorganic halide.

2. The process of claim 1 wherein the organic acid is acetic acid, the inorganic chloride compound is hydrochloric acid, and the 1-carbohydrocarbyloxy-2-keto-4-hydroxy-5-cyclopentene and 4-ketocyclopentene compounds correspond to the formula:

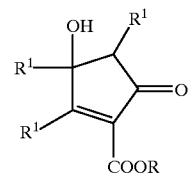 and 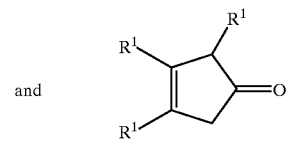

wherein, R is C$_{1-20}$ hydrocarbyl; and

R$^1$ independently each occurrence is hydrogen, hydrocarbyl, silyl, germyl, halide, or halo-substituted hydrocarbyl, said R$^1$ group having up to 40 atoms not counting hydrogen atoms, and optionally two or more of the foregoing adjacent R$^1$ groups may together form a divalent derivative thereby forming a saturated or unsaturated fused ring or multiple ring system, and further optionally one or more of the carbons of R$^1$ in any of the so formed rings may be replaced by a nitrogen, boron, phosphorus or sulfur atom.

3. The process of claim 1 wherein 2,3-dihydro-2-oxo-1H-cyclopenta(I)phenanthrene is prepared from a C$_{1-20}$ alkyl 3,3a-dihydro-3a-hydroxy-2-oxo-2H-cyclopenta(I)phenanthrene-1-carboxylate.

* * * * *